United States Patent [19]

Miller et al.

[11] 4,432,013
[45] Feb. 14, 1984

[54] METHOD AND APPARATUS FOR COMPARING DATA SIGNALS IN A CONTAINER INSPECTION DEVICE

[75] Inventors: John W. V. Miller, Toledo, Ohio; John W. Juvinall, Ottawa Lake, Mich.

[73] Assignee: Owens-Illinois, Inc., Toledo, Ohio

[21] Appl. No.: 323,793

[22] Filed: Nov. 23, 1981

[51] Int. Cl.$^3$ .............................................. H04N 7/18
[52] U.S. Cl. .................................... 358/106; 250/563; 356/434
[58] Field of Search ................ 358/106, 221; 250/562, 250/563, 572, 223 B; 356/237, 238, 240, 430, 431, 434; 209/526, 528

[56] References Cited

U.S. PATENT DOCUMENTS

| | | | |
|---|---|---|---|
| 3,863,248 | 1/1975 | Deschenes et al. | 340/347 DD |
| 3,949,162 | 4/1976 | Malueg | 358/221 |
| 3,958,127 | 5/1976 | Faulhaber et al. | 250/563 |
| 4,136,930 | 1/1979 | Gomm et al. | 358/106 |
| 4,274,747 | 6/1981 | Van Beeck et al. | 356/434 |
| 4,292,672 | 9/1981 | Southgate | 356/239 |
| 4,293,877 | 10/1961 | Tsunekawa et al. | 358/221 |

Primary Examiner—Joseph A. Orsino, Jr.
Attorney, Agent, or Firm—Gerald T. Welch; Myron E. Click

[57] ABSTRACT

The present invention relates to an apparatus and method for generating a comparison signal representing the deviation between two analog video signals representing light received from particular inspection points on an object being inspected. The comparison signal is generated with a magnitude representing the ratio between the values of the two video signals. The ratio is calculated with the one of the two video signals having the larger magnitude as the denominator. In order to calculate the ratio, the present invention first converts the two analog video signals to digital form and then determines the log of each of digitized video signal. Next, the negative difference between the two log signals is determined. The negative difference is then exponentiated to determine the ratio.

18 Claims, 4 Drawing Figures

METHOD AND APPARATUS FOR COMPARING DATA SIGNALS IN A CONTAINER INSPECTION DEVICE

CROSS-REFERENCE TO RELATED APPLICATION

The present invention is related in subject matter to the sidewall inspection device described in U.S. patent application Ser. No. 205,054, filed Nov. 7, 1980, in the name of John W. V. Miller and entitled "METHOD AND APPARATUS FOR RAPIDLY EXTRACTING SIGNIFICANT DATA FROM A SPARSE OBJECT", and to the sidewall inspection device described in U.S. patent application Ser. No. 218,996, filed Dec. 22, 1980, in the name of John W. Juvinall and entitled "METHOD AND APPARATUS FOR COMPARING DATA SIGNALS IN A CONTAINER INSPECTION DEVICE", both applications assigned to the assignee of the present application.

BACKGROUND OF THE INVENTION

1. Field of the Invention

The present invention relates in general to sidewall inspection devices for containers and in particular to a method and apparatus for comparing individual video data signals from an inspection of a container, such as a glass bottle.

2. Description of the Prior Art

The use of optical scanning devices for inspecting the sidewalls of containers is well known. Numerous devices, such as those shown in U.S. Pat. Nos. 3,708,680 and 3,716,136, have circuitry including means for receiving and interpreting light passed through or directed onto an item under inspection. Such devices incorporate either a visual display for comparison of the item or employ a device capable of producing a resistance proportional to the intensity of light directed thereon. Whether the output of such a device is visual or electrical in nature, it is eventually compared against a model to determine if the item under inspection is suitable as to size and construction and is without flaws, cracks, or foreign objects. Such devices are each intended to provide an automated inspection means for checking, as in a moving column of bottles with either single or multiple objects in that moving column.

U.S. Pat. No. 3,877,821 discloses an apparatus having a scanning array that is serially interrogated to generate a train of pulses having amplitudes representing the light transmitted through an object under inspection. Adjacent pulses are compared to generate pulses having amplitudes which represent the difference in pulse amplitudes. The difference pulses can be utilized to indicate a defect in the object being inspected. U.S. Pat. No. 3,942,001 discloses an apparatus for detecting the presence of extraneous matter or cracks in translucent containers. A beam of light is projected through the container to generate an inspection signal which is compared with an acceptance signal. The acceptance signal amplitude is varied in accordance with the position of the spot beam with respect to the container.

One of the problems associated with prior art inspection devices is the sensitivity of the inspection device to general light variations across the container. For example, in the above discussed U.S. Pat. No. 3,877,821, the amplitude of the difference pulse varies in accordance with the intensity of the light. Thus, if the intensity of light varies across the container, a difference pulse representing one type of defect in one portion of the container may be different in amplitude than a difference pulse representing a similar defect in another portion of the container subject to a different intensity of light.

SUMMARY OF THE INVENTION

The present invention is concerned with a method and apparatus for comparing video data signals generated from an inspection of an object in which the comparison is insensitive to general light variations across the object. A light source and camera are utilized to generate a series of video signals each having a magnitude corresponding to the amount of light received from a particular point of inspection, or pixel, on the object. Successive video signals represent adjacent pixels on the object.

A comparison circuit is responsive to the video signals for generating a comparison signal representing the magnitude deviation between two analog video signals. In accordance with the present invention, the comparison signal is generated with a magnitude representing the ratio between the two video signals. The ratio is calculated by converting each of the two analog video signals to digital form before any calculations are performed. Thereafter, the desired ratio can be calculated by digital techniques. By first converting the analog video signals to digital form, the calculations performed by the comparison circuit of the present invention are not subject to component variations and the drift associated with analog comparator circuits.

In the preferred embodiment of the invention, the comparison circuit utilizes an A/D converter to convert the analog video signals into digital form. A latch is utilized to store one of the digitized video signals while another video signal is supplied to the A/D converter. The outputs of the latch and the A/D converter are supplied to individual ROM log tables each of which generate an output signal representing the log of the respective input signal. The difference between the two log output signals is determined by an adder which generates an output signal as an input to a ROM inverse log table. The ROM inverse log table exponentiates the difference signal to generate a comparison signal which represents the ratio between the two video signals. The ROM inverse log table is programmed to exponentiate the negative difference between the two log output signals such that the ratio is generated with a value equal to or less than one.

The comparison circuit according to the present invention also provides a means for offsetting each of the incoming analog video signals by a predetermined amount representing the dark signal level of the series of video signals. The camera utilized in conjunction with the comparison circuit generates a portion of the series of video signals at the dark signal level. The comparison circuit is responsive to the video signals at the dark signal level for setting a counter at an amount which is proportional to the dark signal level. A D/A converter is provided to convert the output of the counter to an analog offset signal. The analog offset signal is then combined with the incoming video signals. By offsetting the incoming video signals, the comparison circuit is able to utilize the full range of the A/D converter and thereby increase the accuracy of the calculated ratio.

DESCRIPTION OF THE PREFERRED EMBODIMENT

Figure 1:
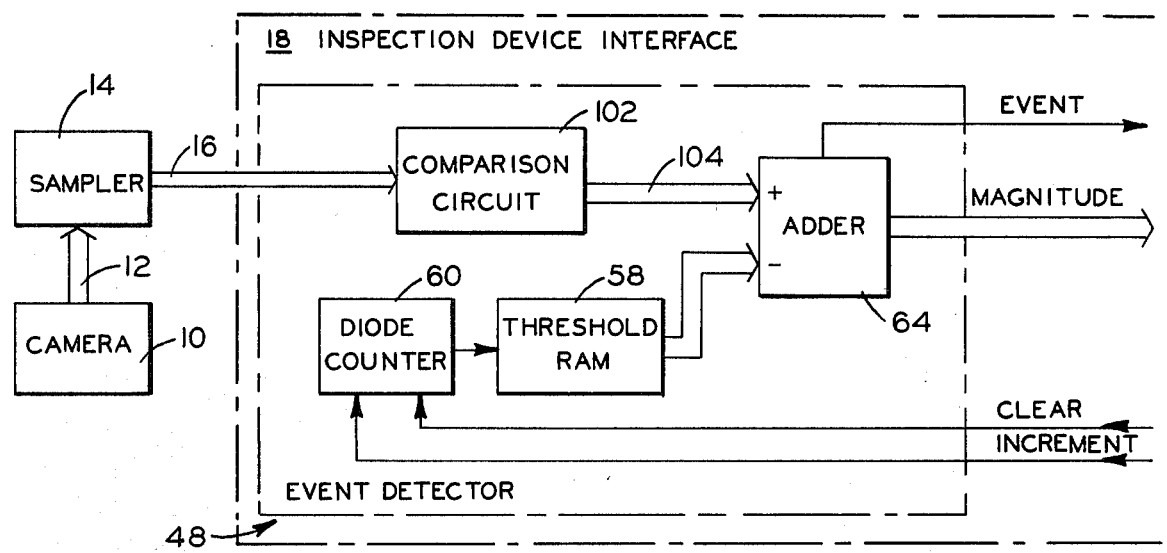
FIG. 1 is a block diagram of a portion of an inspection device which incorporates the present invention.

Referring to FIG. 1, there is shown in block diagram form a portion of a sidewall inspection device for detecting defects in objects such as containers. Although FIG. 1 will be discussed briefly, a more detailed description of those elements shown in the drawings with reference numerals below 100 and the remaining portion of the inspection device not shown in FIG. 1 can be found in the above-identified U.S. patent application Ser. No. 205,054. It should be noted that the reference numerals herein which are less than 100 correspond directly to elements which have been discussed in detail in U.S. patent application Ser. No. 205,054.

Figure 2:
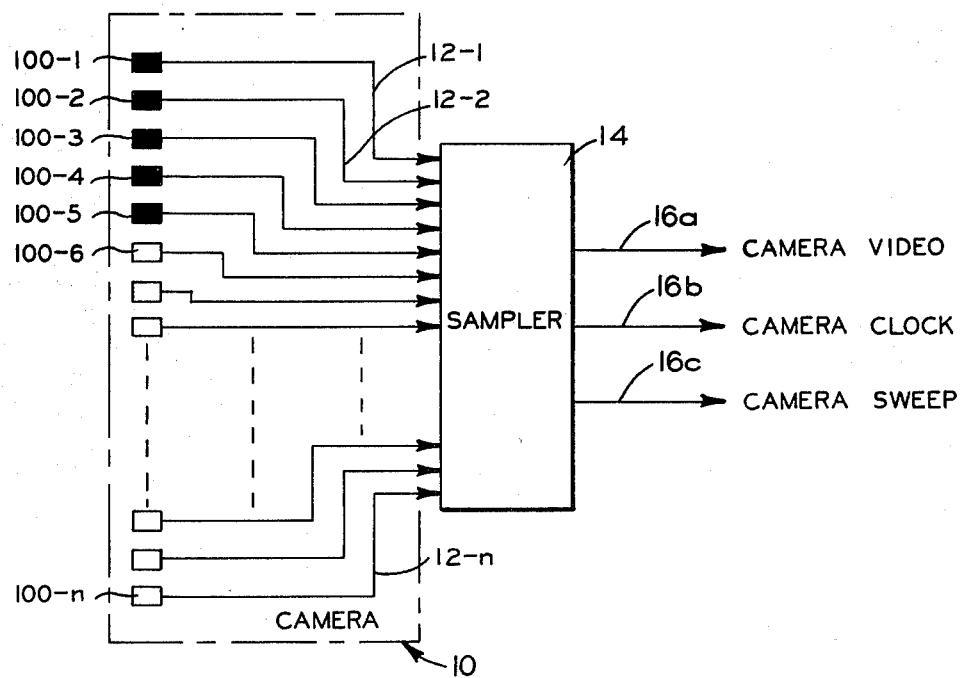
FIG. 2 is a more detailed block diagram of the camera unit and sampler of FIG. 1.

In FIG. 1, an object, such as a glass bottle (not shown), is scanned by a camera 10. The camera 10 generates a plurality of signals on lines 12 proportional in magnitude to the amount of light received from the glass bottle. In the preferred embodiment of the invention, a light source (not shown) directs a beam of light through the glass bottle under inspection and into the camera 10. As shown in FIG. 2, the camera 10 includes a plurality of photosensitive devices, such as photodiodes 100-1 through 100-n, which are vertically arranged in a linear array. It has been found that a linear array of two hundred fifty-six photodiodes yields satisfactory results. A photodiode is a variable resistance device that will pass a voltage proportional to the amount of light falling thereon.

Each photodiode receives light which has passed through a different inspection point on the bottle. An inspection point is typically referred to as a pixel. If a flaw, crack, or foreign object is contained in the bottle, then the light passing through the corresponding pixel of the bottle will be partially blocked or reflected and the corresponding photodiode will register a different intensity of light than had no defect been present.

The signals from the photodiodes 100-1 through 100-n of the camera 10 are supplied to a sampler 14 on a plurality of lines 12-1 through 12-n, respectively. Each of the photodiodes is sampled in a sequential order to produce a series of video pulse signals on lines 16 which represent the amount of light which has passed through the bottle under inspection at points corresponding to the vertical array of the photodiodes. The sampler 14 is a device well known in the art. By rotating the bottle under inspection relative to the camera 10, a plurality of different sweeps can be made, each sweep inspecting a different portion of the bottle. It has been found that about three hundred seventy-five to four hundred different sweeps will sufficiently cover an average bottle and ensure an accurate inspection. Thus, the sampler 14 generates a plurality of video signals series on the lines 16 each signal having a magnitude proportional to the amount of light passing through the corresponding point on the bottle.

As shown in FIG. 2, the analog camera video signal is generated on a line 16a. In addition to the camera video signal on the line 16a, the sampler 14 also generates a camera clock signal on a line 16b and a camera sweep signal on a line 16c. The camera sweep signal consists of a pulse representing the beginning of each camera sweep, while the camera clock signal consists of a pulse train with each pulse signalling the transmission of a video pulse signal on the line 16a.

The video signals generated by the sampler 14 on the lines 16 are an input to an event detector 48 which represents a portion of an inspection device referred to as an inspection device interface 18. The interface 18, which is discussed in detail in the above-identified U.S. patent application Ser. No. 205,054, functions to rapidly extract significant data from the sweep of the glass bottle in a manner which is suitable for computer analysis.

The event detector 48 includes a comparison circuit 102 which receives the analog video signals on the lines 16 and generates a digital comparison signal on lines 104 to an adder 64. The comparison circuit 102 functions to generate a comparison signal on lines 104 representing the deviation between two analog video signals on the lines 16.

The event detector 48 includes a threshold random access memory (RAM) 58 for storing a plurality of threshold signals. Each threshold signal stored in the RAM 58 corresponding to a specific comparison signal generated by the comparison circuit 102. A diode counter 60 is utilized to select the individual threshold signal from the RAM 58 which corresponds to the present comparison signal generated by the circuit 102. The diode counter 60 can be reset to zero by a CLEAR signal and can be incremented by an INCREMENT signal. Both the CLEAR signal and the INCREMENT signal can be generated by a control logic unit 54 (not shown) of the interface 18.

The signal from the threshold RAM 58 is supplied to a complementary input of the adder 64 where it is combined with the comparison signal of the lines 104. When the magnitude of the comparison signal on the lines 104 exceeds the magnitude of the corresponding threshold signal, the adder 64 generates an EVENT signal to inform the control logic unit 54 of the interface 18 that the detector 48 has detected a defect. The adder 64 can also generate a MAGNITUDE signal to inform the control logic unit 54 of the interface 18 as to the difference in magnitude between the comparison signal on the line 104 and the corresponding threshold signal.

Figures 3, 4:
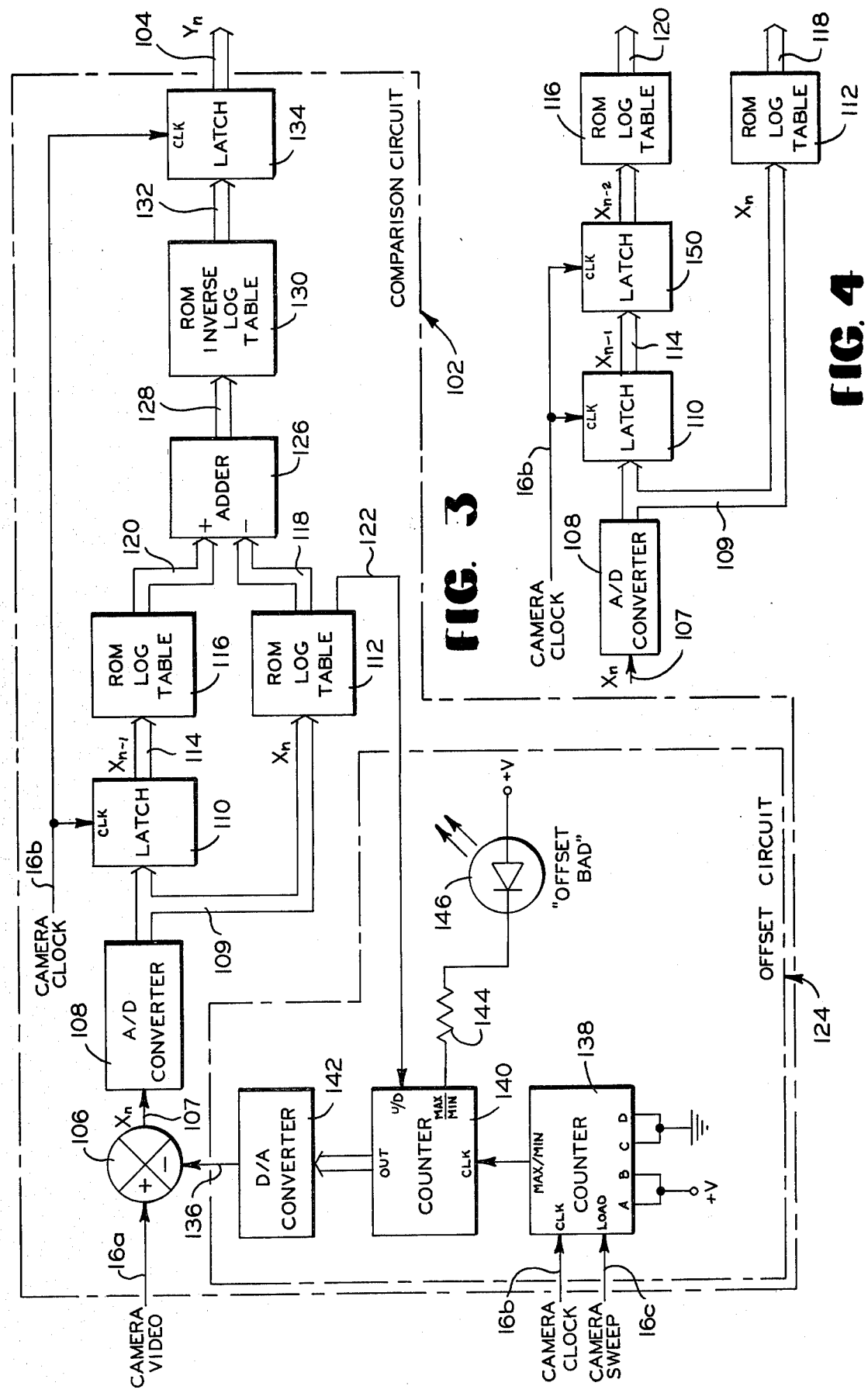
FIG. 3 is a block diagram of the comparison circuit of FIG. 1 according to the present invention.
FIG. 4 is a block diagram of an alternate embodiment of a portion of the circuit of FIG. 3.

There is shown in FIG. 3 a block digram of the comparison circuit 102 according to the present invention. Basically, the comparison circuit according to the present invention functions to generate a comparison signal on lines 104 which is representative of the magnitude difference between two video signals generated on the line 16a. As will be discussed, the method according to the present invention results in a comparison signal which is insensitive to ambient light variations across the bottle.

In FIG. 3, the analog camera video signal on the line 16a is supplied to a first input of a summing junction 106 having an output line 107 connected to supply an offset video signal $X_n$ to an input of an A/D converter 108. The A/D converter 108 converts the analog video signal $X_n$ into digital form and supplies the digitized video signal on lines 109 as an input to a latch 110 and also as an input to a ROM log table 112. The latch 110 has a clock (CLK) input connected to receive the camera clock signal on the line 16b. The output signal $X_{n-1}$ of the latch 110 is generated on lines 114 as an input to a second ROM log table 116. Both the ROM log tables 112 and 116 function to generate digital output signals on lines 118 and 120 respectively representative of the log of the respective input signal. As will be discussed, the ROM log table 112 also generates a polarity logic signal on a ling 122 which is representative of the polarity of the incoming offset video signal $X_n$. The polarity logic signal on the line 122 is utilized by an offset circuit 124 for determining an offset signal which is combined with the incoming camera video signals.

The outputs of the ROM log tables 112 and 116 are supplied as inputs to an adder 126 which functions to generate a digital output signal on lines 128 representing the difference between the two incoming log signals. The difference between the two log signals on the lines 120 and 118 represents the log of the ratio between the digitized camera video signals on the lines 114 and 109. The difference log signal on the lines 128 is supplied as an input to a ROM inverse log table 130 which functions to exponentiate the signal on the lines 128 to generate the comparison signal on the lines 132 as an input to a latch 134. The latch 134 has a clock (CLK) input connected to receive the camera clock signal on the line 16b and an output connected to supply a comparison signal $Y_n$ to the adder 64 on the lines 104.

The ROM inverse log table 130 is programmed to exponentiate the negative value of the difference log signal on the lines 128. Thus, if the difference log signal on the lines 128 is of a positive value, the ROM table 130 will first convert the signal to a negative value before performing the exponentiating operation. This results in a comparison signal having a value less than or equal to one and thus represents a ratio with the larger of two video signals in the denominator.

The offset circuit 124 functions to generate an offset signal on a line 136 as a second input of the summing junction 106. Basically, the offset signal on the line 136 is generated with a magnitude representing the dark signal level generated by a portion of the photodiodes 100 of the camera 10.

The offset circuit 124 includes a counter 138 having a clock (CLK) input connected to receive the camera clock signal on the line 16b and a LOAD input connected to receive the camera sweep signal on the line 16c. The counter 138 has preset inputs A and B connected to a +V power supply (not shown) and preset inputs C and D connected to the ground potential. The MAX/MIN output of the counter 138 is connected to a clock (CLK) input of a counter 140 having an up/down (U/D) input connected to receive the polarity logic signal on the line 122. The output of the counter 140 is supplied as an input to a D/A converter 142 having an output connected to generate the offset signal on the lines 136. The counter 140 has a MAX/MIN output connected to the cathode of an "offset bad" LED 146 through a resistor 144. The anode of the LED 146 is connected to the +V power supply.

In order to determine the magnitude of the dark signal level, the present invention requires that at least one of the photodiodes 100 of the camera 10 be "blacked out". This is accomplished by masking out selected photodiodes in the camera 10. For example, in FIG. 2 the photodiodes 100-1 through 100-5 are schematically represented as being "blacked out". The camera sweep signal on the line 16c is then generated at the beginning of each scanner sweep. The generation of the camera sweep signal on the line 16c causes the counter 138 to load the present count at preset inputs A, B, C and D into the counter. In FIG. 3, the preset count has a value of three. Once the camera sweep signal is received by the counter 138, the counter will count down in response to each camera clock signal until the counter reaches zero. At this time, the counter 138 will generate a signal at the MAX/MIN output which is supplied to the clock input of the counter 140. The counter 140 will then be incremented or decremented by one count in accordance with the level of the polarity logic signal on the line 122.

Since the camera sweep occurs immediately prior to the generation of the camera video signal corresponding to the photodiode 101-1 and since the preset input of the counter 138 is set at three, the particular camera video signal which is being supplied to the ROM log table 112 when the counter 138 reaches zero will correspond to the photodiode 100-3. If the offset video signal $X_n$ generated by the photodiode 100-3 on the line 109 is greater than zero, the ROM log table 112 will generate a polarity logic signal on the line 122 which causes the counter 140 to count up in response to the MAX/MIN output signal from the counter 138. Thus, when the offset video signal corresponding to the photodiode 100-3 is of a positive polarity, the MAX/MIN output of the counter 138 will cause the counter 140 to be incremented to increase the value of the offset signal. Conversely, if the offset video signal on the line 109 is of a negative polarity, the polarity logic signal on a line 22 will cause the counter 140 to be decremented and thus reduce the value of the offset signal.

Each sweep of the scanner 14 thus causes the counter 140 to be either incremented or decremented depending on the polarity of the input signal $X_n$ to the A/D converter 108. During the initial start up of the comparison circuit 102, a predetermined number of sweeps will typically be required in order for the magnitude of the offset signal on the line 136 to reach the dark signal magnitude. Thereafter, the offset circuit 124 will continue to monitor the dark signal level from one of the selected photodiodes and update the count of the counter 140 accordingly. If the count of the counter 140 should reach the maximum allowable count, the counter generates a MAX/MIN signal near ground potential to light the "offset bad" LED 146 and signal the operator that the offset signal on the line 136 may not properly represent the actual dark signal level.

In comparing the method of adjacent pixel differencing to the method according to the present invention, the advantages of the present invention can be readily seen. In the method of adjacent pixel differencing, the comparison signal $Y_n = X_n - X_{n-1}$. Thus, if $X_n$ has a magnitude of four and $X_{n-1}$ has a magnitude of three, the comparison signal $Y_n$ would equal one for a given amount of illumination. However, if the illumination were increased twofold, the comparison signal would have a value of two. Thus, in the prior art method of pixel differencing, the ambient light across the bottle had to remain relatively uniform such that similar responses were obtained for similar defects. The present invention permits a gradual illumination variation across the bottle without affecting the value of the comparison signal. For example, in the method of the present invention, if the $X_n$ and $X_{n-1}$ signals are equal to four and three respectively, the comparison signal $Y_n$ would equal $\frac{3}{4}$. If the illumination were increased such that for the same defect $X_n$ had a value of eight and $X_{n-1}$ had a value of six, the comparison signal $Y_n$ would still equal ¾. Thus, the present method results in the same comparison signal value for the same defect, regardless of the ambient light level common to both $X_n$ and $X_{n-1}$ pixels.

In addition to providing a comparison method which is insensitive to general light variations across the container, the present invention also utilizes digital circuitry within the comparison circuit such that the calculation of the desired ratio is not subject to drifting and component variations associated with analog comparator circuits. Moreover, the basically digital offset circuit provides an effective means for offsetting the incoming analog camera video signal such that the full range of the A/D converter 108 can be utilized.

The circuit shown in FIG. 3 is designed to generate a comparison signal representing the ratio between two successive camera video signals. However, in some instances, it may be desirous to compare camera video signals which are not successive. For example, FIG. 4 illustrates a modification to FIG. 3 wherein a second latch 150 is connected between the output of the latch 110 and the input of the ROM log table 116. The latch 150 has a clock (CLK) input connected to receive the camera clock signal on the line 16b. Such an arrangement permits the comparison circuit to compare alternately generated camera video signals by generating a comparison signal representing the ratio between the $X_n$ and the $X_{n-2}$ video signals.

One of the advantages of comparing alternate video signals rather than successive video signals is that the comparison signal generated as a result of the comparison between alternate video signals may more accurately represent a detected defect. For example, if a stone is located within a particular pixel on the bottle, the amount of light received from an inspection of that pixel will be reduced. However, typically the light received from an inspection of an adjacent pixel will also be affected by the stone, such that this level is also reduced from the normal light level. On the other hand, an inspection of a pixel located two pixels away from the pixel having the stone is less likely to be significantly affected by the stone. Consequently, a comparison between the alternate video signals may more accurately reflect the presence of the stone in the glass.

The components shown in FIG. 3 and FIG. 4 are all commercially available. The A/D converter 108 can be a model TDC-1001J available from TRW Products of Redondo Beach, Calif. The latches 110, 134, and 150 can each be an LS374 latch, the ROM log tables 112 and 116 can be model number 74S471 PROMs, the adder 126 can be constructed of model number 74283 four bit binary adders, the ROM inverse log table 130 can be a model number 2732A EPROM, and the counters 138 and 140 can be constructed of model number 74191 UP/DOWN binary counter, all of which are available from Texas Instruments, Inc., of Dallas, Tex. The D/A converter 142 can be a model number DAC1222 12 bit D/A converter available from National Semiconductors of Santa Clara, Calif.

It should be noted that the present invention encompasses the method of dividing the value of one video pixel signal by the value of a second video pixel signal to generate a comparison signal which represents the ratio of the two signals. However, from a practical standpoint, it is generally not desirous to have a ratio which can cover a wide range of values. This is especially true where a limited range A/D converter is used to convert an analog signal into digital form. For example, such a ratio may result in relatively large values if the denominator is significantly smaller than the numerator. Accordingly, the comparison circuit of the present invention includes means for calculating the ratio with the larger of the two video signals in the denominator, thus ensuring that the ratio will be equal to or less than one. This makes the method of the present invention readily adaptable to computer-controlled digital circuits.

The method of the present invention is also readily adapted for use with a camera generating a series of digitized video signals. In such a use, the A/D converter 108 of FIG. 3 would not be required and the camera output signals could be supplied directly to the latch 110 and the ROM log table 112.

In accordance with the provisions of the patent statutes, the principle and mode of operation of the invention have been explained and illustrated in its preferred embodiment. However, it must be understood that the invention may be practiced otherwise than as specifically illustrated and described without departing from its spirit or scope.

What is claimed is:

1. In an apparatus for detecting defects in an object including a camera for generating a series of analog video signals each having a magnitude proportional to an amount of light received from a particular point of inspection on the object, a circuit for generating a comparison signal representing a magnitude difference between two of the analog video signals, said circuit comprising: converter means responsive to the two analog video signals for converting the magnitude values of the analog signals to digital form and comparison means responsive to the digitized video signals for generating a comparison signal having a magnitude representing a ratio of the one of the two video signals having the smaller magnitude to the other one of the two video signals having the later magnitude, said comparison means including a first ROM log table responsive to one of said two digitized video signals for generating a first log signal representing the log of the value of said one video signal, a second ROM log table responsive to the other one of said two digitized video signals for generating a second log signal representing the log of the value of said other video signal, means responsive to said first and second log signals for generating an output signal representing the difference between the values of said first and second log signals, and a ROM inverse log table responsive to said output signal for generating said comparison signal.

2. The circuit according to claim 1 wherein the two video signals being compared represent light received from adjacent points of inspection on the object.

3. The circuit according to claim 1 wherein the two video signals being compared represent non-adjacent points of inspection on the object.

4. The circuit according to claim 1 including means for storing one of the two digitized video signals.

5. The circuit according to claim 1 wherein said means for generating an output signal generates said output signal with a magnitude representing the negative difference between the values of said first and second log signals.

6. The circuit according to claim 1 including an offset means responsive to said series of video signals for generating an offset signal representing a dark signal magnitude of the series of video signals.

7. The circuit according to claim 6 including means responsive to said offset signal for offsetting the analog video signals by said dark signal magnitude.

8. The circuit according to claim 6 wherein at least a selected one of said series of analog video signals is generated at said dark signal magnitude and wherein said offset means includes means responsive to said selected one video signl for storing a value representing said dark signal magnitude.

9. The circuit according to claim 8 wherein said means for storing is a counter responsive to said selected one digitized video signal for storing a count representing said dark signal magnitude.

10. The circuit according to claim 9 wherein said offset means includes a D to A converter having an input connected to the output of said counter for generating said offset signal in analog form.

11. A method of generating a comparison signal representing a magnitude difference between two analog video signals generated by an apparatus for detecting defects in an object including a camera for generating a series of analog video signals each having a magnitude proportional to an amount of light received from a particular point of inspection on the object, comprising the steps of:
  (a) converting the two analog video signals to digital form;
  (b) determining a ratio between the values of the two digitized video signals so that the ratio has a value less than or equal to one by
  (b1) determining the log of the value of each of the two digitized video signals,
  (b2) determining the negative difference value between the two log values, and
  (b3) exponentiating the negative difference value to determine the ratio; and
  (c) generating the comparison signal having a magnitude equal to said ratio.

12. The method according to claim 11 including a step of offsetting the values of the two analog video signals by an amount representing a dark signal magnitude of the series of video signals.

13. The method according to claim 11 wherein said two video signals being compared represent light received adjacent points of inspection on the object.

14. The method according to claim 11 wherein said two video signals being compared represent light received from non-adjacent points of inspection on the object.

15. In an apparatus for detecting defects in an object including a camera for generating a series of digitized video signals each having a magnitude proportional to an amount of light received from a particular point of inspection on the object, a circuit for generating a comparison signal representing a magnitude difference between two of the digitized video signals, and circuit comprising: comparison means responsive to the two digitized video signals for generating a comparison signal having a magnitude representing a ratio of the one of the two video signals having the smaller magnitude to the other one of the two video signals having the larger magnitude, said comparison means including a first ROM log table responsive to one of said two digitized video signals for generating a first log signal representing the log of the value of said one video signal, a second ROM log table responsive to the other one of said two digitized video signals for generating a second log signal representing the log of the video of said other video signal, means responsive to said first and second log signals for generating an output signal representing the difference between the values of said first and second log signals, and a ROM inverse log table responsive to said output signal for generating said comparison signal.

16. The circuit according to claim 15 including means for storing one of said two digitized video signals.

17. An inspection apparatus including a means for generating a series of digital video signals each representing an amount of light received from a particular point of inspection on an object and comparison means responsive to the digital video signals for generating a comparison signal having a magnitude representing a ratio of the one of two of the video signals having the smaller magnitude to the other one of the two video signals having the larger magnitude, said means for generating said comparison means including a first ROM log table responsive to one of said two digitized video signals for generating a first log signal representing the log of the value of said one video signal, a second ROM log table responsive to the other one of said two digitized video signals for generating a second log signal representing the log of the value of said other video signal, means responsive to said first and second log signals for generating an output signal representing the difference between the values of said first and second log signals, and a ROM inverse log table responsive to said output signal for generating said comparison signal.

18. An inspection apparatus according to claim 17 wherein said means for generating an output signal generates said output signal with a magnitude representing the negative difference between the values of said first and second log signals.

* * * * *